United States Patent
Hashiba (10) Patent No.: US 9,089,262 B2
(45) Date of Patent: Jul. 28, 2015

(54) MEDICAL SYSTEMS, DEVICES AND METHODS FOR SUTURING PERFORATIONS

(75) Inventor: Kiyoshi Hashiba, Sao Paulo (BR)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 780 days.

(21) Appl. No.: 12/770,012

(22) Filed: Apr. 29, 2010

(65) Prior Publication Data

US 2010/0280530 A1 Nov. 4, 2010

Related U.S. Application Data (60) Provisional application No. 61/174,583, filed on May 1, 2009.

(51) Int. Cl.
*A61B 17/04* (2006.01)
*A61B 1/018* (2006.01)
*A61B 1/00* (2006.01)
*A61B 17/00* (2006.01)
*A61B 17/062* (2006.01)
*A61B 19/00* (2006.01)

(52) U.S. Cl.
CPC .............. *A61B 1/018* (2013.01); *A61B 1/0008* (2013.01); *A61B 17/0057* (2013.01); *A61B 17/0469* (2013.01); *A61B 17/0625* (2013.01); *A61B 17/0482* (2013.01); *A61B 17/0487* (2013.01); *A61B 2017/00663* (2013.01); *A61B 2019/4857* (2013.01)

(58) Field of Classification Search
CPC ........... A61B 17/0057; A61B 17/0469; A61B 17/0482; A61B 17/062; A61B 17/0625; A61B 1/0008; A61B 1/018
USPC .......... 606/139, 144, 148, 140–143, 145–147
See application file for complete search history.

(56) References Cited

U.S. PATENT DOCUMENTS

| | | | |
|---|---|---|---|
| 1,037,864 | A | 9/1912 | Carlson |
| 2,199,025 | A | 4/1940 | Conn |

(Continued)

FOREIGN PATENT DOCUMENTS

| | | |
|---|---|---|
| DE | 19944236 | 3/2001 |
| EP | 1946707 | 7/2008 |

(Continued)

OTHER PUBLICATIONS

International Search Report and Written Opinion for PCT/US2010/032929.
International Search Report and Written Opinion for PCT/US2008/073082.
International Preliminary Report on Patentability for PCT/US2008/073082.
International Search Report and Written Opinion for PCT/US2009/030030.
International Preliminary Report on Patentability for PCT/US2009/030030.

*Primary Examiner* — Alexander Orkin
(74) *Attorney, Agent, or Firm* — Brinks Gilson & Lione (57) ABSTRACT

Medical systems, devices and methods are disclosed for suturing a perforation in tissue, that may be employed endoscopically and/or laparoscopically, and that offer simple, reliable and controllable placement of sutures around a perforation for complete closure thereof. One embodiment of the medical system generally includes an endoscope, an endcap, an elongated side tube, a needle, a suture and a retrieval device. The endcap is fitted to a distal end of the endoscope. The elongated side tube defines a side channel and is connected to the endcap. The needle has a shaft and a needle tip detachably connected to a distal end of the shaft. The needle is sized to be translated through the side channel of the side tube. The suture is attached to the needle tip. The retrieval device is sized to be translated through a working channel of the endoscope and retrieve the needle tip.

13 Claims, 7 Drawing Sheets

(56) References Cited

U.S. PATENT DOCUMENTS

| | | | |
|---|---|---|---|
| 2,880,728 A | 4/1959 | Rights | |
| 3,470,875 A | 10/1969 | Johnson | |
| 4,235,238 A | 11/1980 | Ogiu et al. | |
| 4,236,470 A | 12/1980 | Stenson | |
| 4,448,194 A | 5/1984 | DiGiovanni et al. | |
| 4,749,114 A | 6/1988 | Green | |
| 4,773,420 A | 9/1988 | Green | |
| 4,821,939 A | 4/1989 | Green | |
| 4,890,615 A | 1/1990 | Caspari et al. | |
| 5,015,250 A | 5/1991 | Foster | |
| 5,053,043 A | 10/1991 | Gottesman et al. | |
| 5,203,787 A | 4/1993 | Noblitt et al. | |
| 5,318,221 A | 6/1994 | Green et al. | |
| 5,333,624 A | 8/1994 | Tovey | |
| 5,356,424 A | 10/1994 | Buzerak et al. | |
| 5,366,480 A | 11/1994 | Corriveau et al. | |
| 5,368,599 A | 11/1994 | Hirsch et al. | |
| 5,376,096 A | 12/1994 | Foster | |
| 5,383,882 A | 1/1995 | Buess et al. | |
| 5,389,103 A | 2/1995 | Melzer et al. | |
| 5,395,381 A | 3/1995 | Green et al. | |
| 5,403,329 A | 4/1995 | Hinchcliffe | |
| 5,403,342 A | 4/1995 | Tovey et al. | |
| 5,405,072 A | 4/1995 | Zlock et al. | |
| 5,405,354 A | 4/1995 | Sarrett | |
| 5,417,691 A | 5/1995 | Hayhurst | |
| 5,484,451 A | 1/1996 | Akopov et al. | |
| 5,520,700 A | 5/1996 | Beyar et al. | |
| 5,527,343 A | 6/1996 | Bonutti | |
| 5,554,183 A | 9/1996 | Nazari | |
| 5,571,090 A | 11/1996 | Sherts | |
| 5,573,543 A | 11/1996 | Akopov et al. | |
| 5,683,402 A | 11/1997 | Cosgrove et al. | |
| 5,728,113 A | 3/1998 | Sherts | |
| 5,746,751 A | 5/1998 | Sherts | |
| 5,766,186 A | 6/1998 | Faraz et al. | |
| 5,779,720 A | 7/1998 | Walder-Utz et al. | |
| 5,810,848 A | 9/1998 | Hayhurst | |
| 5,865,791 A | 2/1999 | Whayne et al. | |
| 5,891,159 A | 4/1999 | Sherman et al. | |
| 5,908,428 A | 6/1999 | Scirica et al. | |
| 5,938,668 A | 8/1999 | Scirica et al. | |
| RE36,974 E | 11/2000 | Bonutti | |
| 6,290,674 B1 | 9/2001 | Roue et al. | |
| 6,328,727 B1 | 12/2001 | Frazier et al. | |
| 6,419,669 B1 | 7/2002 | Frazier et al. | |
| 6,491,707 B2 | 12/2002 | Makower et al. | |
| 6,524,234 B2* | 2/2003 | Ouchi | 600/127 |
| 6,572,629 B2 | 6/2003 | Kalloo et al. | |
| 6,582,452 B2 | 6/2003 | Coleman et al. | |
| 6,638,286 B1* | 10/2003 | Burbank et al. | 606/157 |
| 6,641,557 B1 | 11/2003 | Frazier et al. | |
| 6,699,180 B2* | 3/2004 | Kobayashi | 600/127 |
| 6,699,263 B2 | 3/2004 | Cope | |
| 6,712,804 B2 | 3/2004 | Roue et al. | |
| 6,719,763 B2 | 4/2004 | Chung et al. | |
| 6,746,472 B2 | 6/2004 | Frazier et al. | |
| 6,966,916 B2 | 11/2005 | Kumar | |
| 6,997,931 B2 | 2/2006 | Sauer et al. | |
| 7,025,756 B2 | 4/2006 | Frazier et al. | |
| 7,056,325 B1 | 6/2006 | Makower et al. | |
| 7,059,508 B2 | 6/2006 | Shelton, IV et al. | |
| 7,060,024 B2* | 6/2006 | Long et al. | 600/106 |
| 7,087,073 B2 | 8/2006 | Bonutti | |
| 7,115,110 B2 | 10/2006 | Frazier et al. | |
| 7,144,401 B2* | 12/2006 | Yamamoto et al. | 606/144 |
| 7,157,636 B2 | 1/2007 | Hsieh | |
| 7,166,116 B2 | 1/2007 | Lizardi et al. | |
| 7,175,636 B2 | 2/2007 | Yamamoto et al. | |
| 7,357,287 B2 | 4/2008 | Shelton, IV et al. | |
| 7,407,505 B2 | 8/2008 | Sauer et al. | |
| 7,416,554 B2 | 8/2008 | Lam et al. | |
| 7,494,496 B2 | 2/2009 | Swain et al. | |
| 7,575,548 B2* | 8/2009 | Takemoto et al. | 600/104 |
| 7,615,060 B2 | 11/2009 | Stokes et al. | |
| 7,628,796 B2 | 12/2009 | Shelton, IV et al. | |
| 7,731,727 B2 | 6/2010 | Sauer | |
| 7,736,372 B2 | 6/2010 | Reydel et al. | |
| 7,766,925 B2 | 8/2010 | Stokes et al. | |
| 7,828,812 B2 | 11/2010 | Stokes et al. | |
| 7,833,236 B2 | 11/2010 | Stokes et al. | |
| 8,241,204 B2* | 8/2012 | Spivey | 600/106 |
| 2003/0009085 A1 | 1/2003 | Arai et al. | |
| 2003/0181924 A1* | 9/2003 | Yamamoto et al. | 606/144 |
| 2004/0147941 A1* | 7/2004 | Takemoto et al. | 606/144 |
| 2004/0186514 A1 | 9/2004 | Swain et al. | |
| 2005/0015101 A1 | 1/2005 | Gibbens et al. | |
| 2005/0090709 A1* | 4/2005 | Okada et al. | 600/104 |
| 2005/0113851 A1 | 5/2005 | Swain et al. | |
| 2006/0015006 A1 | 1/2006 | Laurence et al. | |
| 2006/0020274 A1 | 1/2006 | Ewers et al. | |
| 2006/0190016 A1* | 8/2006 | Onuki et al. | 606/144 |
| 2006/0282089 A1 | 12/2006 | Stokes et al. | |
| 2007/0213702 A1 | 9/2007 | Kogasaka et al. | |
| 2007/0255296 A1 | 11/2007 | Sauer | |
| 2007/0276424 A1 | 11/2007 | Mikkaichi et al. | |
| 2008/0086153 A1* | 4/2008 | Sakamoto et al. | 606/139 |
| 2008/0114379 A1 | 5/2008 | Takemoto et al. | |
| 2008/0172088 A1 | 7/2008 | Smith et al. | |
| 2008/0185752 A1 | 8/2008 | Cerwin et al. | |
| 2008/0208220 A1 | 8/2008 | Shiono et al. | |
| 2008/0221619 A1 | 9/2008 | Spivey et al. | |
| 2008/0300624 A1 | 12/2008 | Schwemberger et al. | |
| 2008/0300627 A1 | 12/2008 | Measamer et al. | |
| 2008/0319257 A1 | 12/2008 | Sato et al. | |
| 2009/0005800 A1 | 1/2009 | Franer et al. | |
| 2009/0018552 A1 | 1/2009 | Lam et al. | |
| 2009/0062614 A1 | 3/2009 | Adzich et al. | |
| 2009/0076527 A1 | 3/2009 | Miyamoto et al. | |
| 2009/0099578 A1* | 4/2009 | Heneveld et al. | 606/144 |
| 2009/0198212 A1* | 8/2009 | Timberlake et al. | 604/506 |
| 2009/0216081 A1 | 8/2009 | Suzuki et al. | |
| 2009/0222027 A1 | 9/2009 | Sauer | |
| 2009/0222029 A1 | 9/2009 | Gordin et al. | |
| 2009/0306686 A1 | 12/2009 | Ohdaira | |
| 2009/0312773 A1 | 12/2009 | Cabrera et al. | |
| 2009/0312775 A1* | 12/2009 | Gilkey et al. | 606/147 |
| 2010/0010511 A1 | 1/2010 | Harris et al. | |
| 2010/0010512 A1 | 1/2010 | Taylor et al. | |
| 2010/0010520 A1 | 1/2010 | Takahashi et al. | |
| 2010/0030028 A1 | 2/2010 | Cabrera et al. | |
| 2010/0030238 A1 | 2/2010 | Viola et al. | |
| 2010/0030239 A1 | 2/2010 | Viola et al. | |
| 2010/0049213 A1 | 2/2010 | Serina et al. | |
| 2010/0049219 A1 | 2/2010 | Cronin et al. | |
| 2010/0063521 A1 | 3/2010 | Manzo | |
| 2010/0076460 A1 | 3/2010 | Taylor et al. | |
| 2010/0076461 A1 | 3/2010 | Viola et al. | |
| 2010/0094083 A1 | 4/2010 | Taylor et al. | |
| 2010/0094341 A1 | 4/2010 | Raju | |
| 2010/0113873 A1* | 5/2010 | Suzuki et al. | 600/106 |
| 2010/0121140 A1* | 5/2010 | Hashiba et al. | 600/104 |
| 2010/0217282 A1 | 8/2010 | Cabrera et al. | |
| 2010/0262165 A1 | 10/2010 | Kirsch | |
| 2010/0268253 A1 | 10/2010 | Ahlberg et al. | |
| 2010/0274265 A1 | 10/2010 | Wingardner et al. | |

FOREIGN PATENT DOCUMENTS

| | | |
|---|---|---|
| JP | 2004-041733 | 2/2004 |
| WO | WO 93/01750 | 2/1993 |
| WO | WO 01/01868 | 1/2001 |
| WO | WO 2004/103157 | 12/2004 |
| WO | WO 2007/009115 | 1/2007 |
| WO | WO 2007/030753 | 3/2007 |
| WO | WO 2008/045376 | 4/2008 |
| WO | WO 2009/005527 | 1/2009 |

* cited by examiner

MEDICAL SYSTEMS, DEVICES AND METHODS FOR SUTURING PERFORATIONS

CROSS-REFERENCE TO RELATED APPLICATIONS

This application claims the benefit of U.S. Provisional Application Ser. No. 61/174,583 filed on May 1, 2009, entitled "MEDICAL SYSTEMS, DEVICES AND METHODS FOR SUTURING PERFORATIONS," the entire contents of which are incorporated herein by reference.

FIELD OF THE INVENTION

The present invention relates generally to medical systems, devices and procedures for suturing perforations, and more particularly to endoscopically suturing perforations.

BACKGROUND OF THE INVENTION

Openings or perforations in the walls of internal organs and vessels may be naturally occurring, or formed intentionally or unintentionally. In order to permanently close these perforations and allow the tissue to properly heal, numerous medical devices and methods have been developed employing sutures, adhesives, clips, tissue anchors and the like. One such class of devices aims to endoscopically close perforations, such as those within the gastrointestinal tract. Accordingly, various medical devices have been proposed that attach to the endoscope to facilitate perforation closure. Some of these medical devices employ suction to orient the tissue for suturing or anchor placement, while others require the use of tissue graspers or other devices to orient the tissue.

In these medical devices, the particular orientation of the tissue can require the folding of tissue or the overlapping of two or more layers of tissue. To accomplish such tissue orientation and suturing, many of these medical devices are complex and include a host of moving parts, thereby complicating manufacture and increasing the cost of the devices. At the same time, use of these devices by the medical professional can also be complicated and time consuming, resulting in increased procedure times.

BRIEF SUMMARY OF THE INVENTION

The present invention provides medical systems, devices and methods for suturing a perforation in tissue, that may be used endoscopically and/or laparoscopically, and that offer simple, reliable and controllable placement of sutures around a perforation for complete closure thereof. One embodiment of a medical system, constructed in accordance with the teachings of the present invention, generally includes an endoscope, an endcap, an elongated side tube, a needle, a suture and a retrieval device. The endcap is fitted to a distal end of the endoscope. The elongated side tube defines a side channel and is connected to the endcap. The needle has a shaft and a needle tip detachably connected to a distal end of the shaft. The needle is sized to be translated through the side channel of the side tube. The suture is attached to the needle tip. The retrieval device is sized to be translated through a working channel of the endoscope.

According to more detailed aspects, the needle is operable to a deployed configuration wherein the needle tip is laterally spaced from the side tube. The distal end of the needle shaft bends along a curved path in the deployed configuration, and preferably retroflexes. The needle shaft is preferably formed of a resilient material and is biased to the deployed configuration. The needle tip and retrieval device are radially aligned relative to a central axis of the endoscope in the deployed configuration. The distal end of the needle shaft has a curvature such that the needle tip faces proximally in the deployed configuration. One construction of the retrieval device includes a resilient sleeve having teeth, and the sleeve defines an interior passageway sized to receive the needle tip. The needle tip defines a gripping surface, and the teeth are sized and structured to engage the gripping surface. The needle tip may be frictionally fitted to the needle shaft, and may further include an aperture for receiving the suture.

One embodiment of a medical device, constructed in accordance with the teachings the present invention, generally includes an endcap, an elongated side tube, a needle, a suture, and a retrieval device. The endcap defines an interior space sized to receive a distal end of the endoscope. The side tube defines a side channel and is connected to the endcap. The needle has a needle shaft and a needle tip detachably connected to a distal end of the needle shaft. The needle is sized to be translated to the side channel. The needle is operable to a deployed configuration wherein the needle tip is laterally spaced from the side tube. The suture is attached to the needle tip, and the retrieval device is sized to be translated through a working channel of the endoscope for retrieval of the suture and needle tip.

According to more detailed aspects of the medical device, the interior space is sized to provide selective frictional engagement between the endcap and the endoscope. A distal portion of the endcap includes a slot circumferentially aligned with the side tube. The distal portion of the endcap includes a flange extending radially to define a tissue support surface. The flange is positioned proximate the needle when the needle is in the deployed configuration. The needle is further operable to a delivery configuration wherein the needle tip is aligned with the side tube. The needle tip and retrieval device are preferably radially aligned relative to a central axis of the endoscope in the deployed configuration.

A method for suturing a perforation tissue is also provided in accordance with the teachings of the present invention. One embodiment of the method generally includes providing an endoscope having a working channel, and providing a medical device such as the medical device described above. The endcap is fitted to the distal end of endoscope. The endoscope and medical device are introduced to a position proximate the tissue. The needle is operated from the delivery configuration to the deployed configuration such that the needle passes through the tissue. The retrieval device is operated to engage the needle tip, and the needle tip is detached from the shaft.

According to more detailed aspects of the method, the retrieval device is retracted to withdraw the suture through the working channel of the endoscope. The step of introducing the endoscope and medical device may include positioning the side tube proximate the perforation in the tissue. The step of operating the needle includes passing the needle through the tissue in a retrograde manner. The step of operating the needle may include passing the needle through the perforation and then passing the needle through the tissue. The step of detaching the needle tip may include pulling the needle in a proximate direction to assist in detaching the needle tip from the shaft.

BRIEF DESCRIPTION OF THE DRAWINGS

The accompanying drawings incorporated in and forming a part of the specification illustrate several aspects of the present invention, and together with the description serve to explain the principles of the invention. In the drawings.

DETAILED DESCRIPTION OF THE INVENTION

Figure 1:
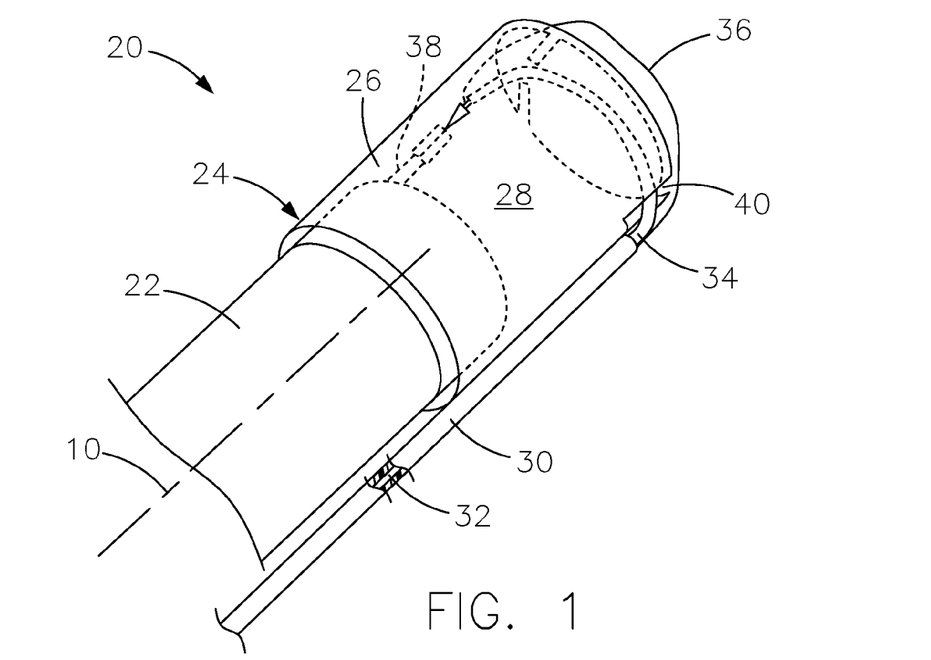
FIG. 1 is a perspective view of a medical system constructed in accordance to the teachings of the present invention.
Figure 2:
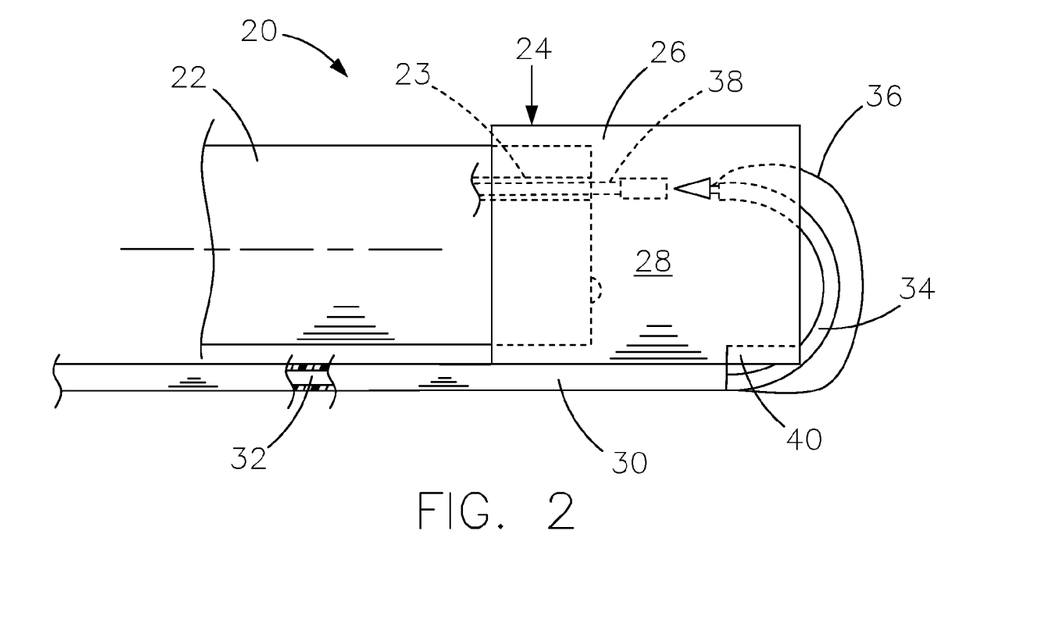
FIG. 2 is a side view of the medical system depicted in FIG. 1.
Figure 3:
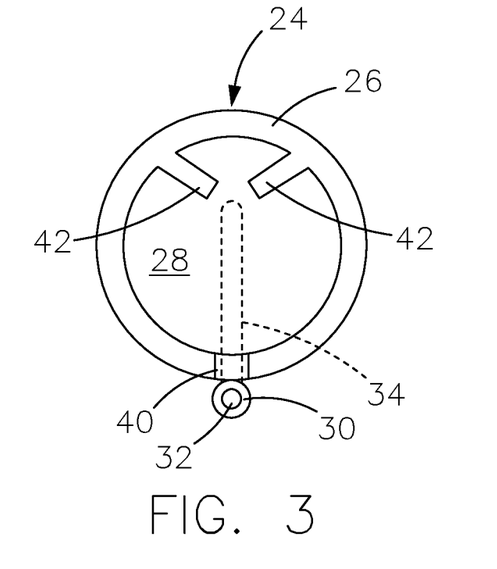
FIG. 3 is a end view of the medical system depicted in FIG. 1.

Turning now to the figures, FIGS. 1-3 depict a medical system 20 for suturing closed a perforation 14 in tissue 12 (shown in FIGS. 11-16), constructed in accordance with the teachings of the present invention. The medical system 20 generally comprises an endoscope 22 and a medical device 24 adapted for use with the endoscope 22. The endoscope 22 generally defines a central axis 10 which extends in a longitudinal direction. The medical device 24 includes an endcap 26 to defining an interior cavity 28 sized to be fitted on a distal end of the endoscope 22. The endcap 26 may be structured to frictionally engage the endoscope 22 for selective retention of the endcap 26 on the endoscope 22, although other means for connecting the endcap 26 to the endoscope 22 may be employed as is known in the art. The endoscope 22 and medical device 24 are therefore adapted to be traversed through the body of a patient in this connected configuration shown in the figures.

The medical device 24 further includes an elongated side tube 30 connected to the endcap 26 and defining a side channel 32. A needle 34 is provided for passing a suture 36 through the tissue 12 to close the perforation 14. The side tube 30 initially guides the needle 34, which is sized to be translated through the side channel 32 of the side tube 30. A retrieval device 38 is sized to be translated through a working channel 23 of the endoscope 22, and is further adapted for cooperating with the needle 34 to retrieve the suture once is has been passed through the tissue 12 proximate the perforation 14. Further details of these components of the medical device 24 will be described hereinbelow.

As shown in FIGS. 1-3, the side tube 30 has been attached to the outer periphery of the endcap 26. It will be recognized that, alternatively, the side tube 30 could be connected to any portion of the endcap 26, including configurations where the endcap 26 defines a channel to which the side channel 32 of the side tube 30 is fitted for communication therebetween. The side tube 30 is preferably connected to the endcap 26 using adhesives, mechanical connectors, plastic welding, or other boding techniques. Alternatively, the endcap 26 and side tube 30 may be unitarily and integrally formed. The side tube 32 extends proximally along the endoscope 22, and therefore has a length similar to the length of the endoscope 22. The endoscope 22 may generally be any scope known to those skilled in the art, and therefore may have various lengths, diameters and functionality.

As will be described in more detail hereinbelow, the needle 34 is generally structured to retroflex in a deployed configuration (generally shown in FIGS. 1-3), thereby allowing the suture 36 to be passed through the tissue 12 in a manner that also places the distal tip 46 of the needle 34 and the suture 36 in a position for retrieval by the retrieval device 38. As shown in FIG. 3, the endcap 26 is structured to facilitate this retroflexing of the needle 34, its passage through the tissue, and its interaction with retrieval device 38 for retrieving the suture 36 from the needle 34 once it has passed through the tissue 12. For example, the endcap 26 defines a slot 40 at its distal end to allow the needle 34 to pass through the slot 40 and into the interior space 28 defined by the endcap 26. Preferably, the slot 40 is circumferentially aligned with the side tube 30 for receiving the needle 34 therein. As best seen in FIG. 3, the endcap 26 further includes one or more flanges 42 (two being shown in the figures) which extend radially outwardly to a position proximate the curved path which is followed by the needle 34 as it retroflexes. The flanges 42 provide support to the tissue 12 for easier puncturing of the tissue 12 by the needle 34, although the flanges 42 need not be employed. The endcap 26 is preferably constructed from a plastic such as polyvinylchloride, polytetrafluoroethylene, polyethylene ether ketone, polycarbonate or other thermoplastics, although other materials such as metals and alloys may readily be employed.

Figure 4:
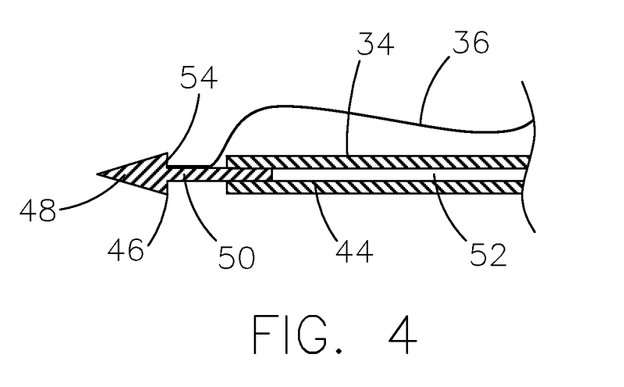
FIG. 4 is a cross-sectional view of a needle forming a portion of the medical system depicted in FIG. 1

Further details of the needle 34 and retrieval device 38, as well as their cooperative interaction, will now be described with reference to FIGS. 4-10. As shown in FIG. 4, the needle 34 generally includes a shaft 44 and a needle tip 46 which is selectively connected to a distal end of the shaft 44. The needle tip 46 generally includes a tapered head 48 for piercing the tissue and a stem 50 connected to the head 48. The shaft 44 defines a needle lumen 52 which is sized to receive the stem 50 of the needle tip 46. Preferably, the stem 50 and needle lumen 52 are sized relative to one another to provide a frictional fit and permits a selective connection and disconnection of needle tip 46 to the shaft 44, although other mechanical means for selectively connecting the needle tip 46 to the shaft 44 may be employed as will be recognized by those skilled in the art.

The needle tip 46 is further connected to the suture 36. Preferably, the suture 36 is connected to the stem 50 of the needle tip, although it can be connected to any portion of the needle tip 46. The suture can be connected by tying, or by using adhesives, mechanical connectors (adjustable loops, clamps, etc.), bonding techniques such as plastic welding, melting, heat bonding and the like. Similarly, either the stem 50 or the suture 36 may be mechanically deformed, such as by crimping or using other techniques, to interconnect the suture 36 and needle tip 46.

The needle 34 is preferably constructed of a material providing sufficient flexibility to traverse the body of a patient through the side tube 30 and along the endoscope 22. At the same time, the needle 34, or at least the distal end of the shaft 44, formed of a flexible but resilient material, thereby enabling the retroflexing of the needle 34 to a deployed configuration as shown in FIGS. 1-3. Preferably, the distal end of the shaft 44 is biased to this deployed configuration, although the distal end of shaft may have shape memory that is temperature dependent and can be activated through the use of fluids or body heat, as is known in the art. Suitable materials for the needle 34 generally include metals such as stainless steel, alloys such as nitinol, plastics such as polyvinylchloride, polyimide, polyamide, polyetherketone and others known to those skilled in the art.

Figure 11:
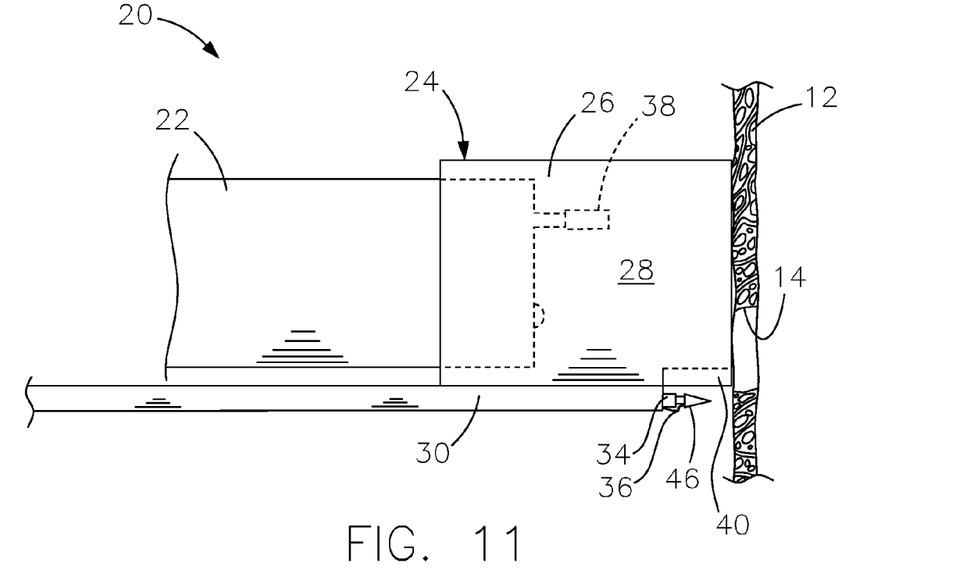
FIGS. 11-15 are side views, partially and cross-section, illustrating a method of employing the medical system depicted in FIG. 1.

Similarly, the side tube 30 guides the needle 34, and when the needle's shaft 44 is biased to the deployed configuration, the side tube straightens out the needle into its delivery configuration (FIG. 11). Accordingly, the side tube 30 is preferably formed of polytetrafluorethylene (PTFE), expanded polytetrafluorethylene (EPTFE), polyethylene ether ketone (PEEK), polyvinylchloride (PVC), polycaerbonate (PC), polyamide including nylon, polyimide, polyurethane, polyethylene (high, medium or low density), and elastomers such as Santoprene™, including multi-layer or single layer constructions with or without reinforcement wires, coils or filaments. The shaft 44 of the needle 34 generally has a sufficient length to pass through the side tube 30 and exit a proximal end thereof (not shown) for manipulation by the medical professional. The side tube has a suitable length for extending from the endcap 26 and along the endoscope 22 to a proximal end thereof (not shown), where a proximal end of the side channel 32 may be accessed by the medical professional for inserting, manipulating and withdrawing the needle 34 therefrom.

Figure 5:
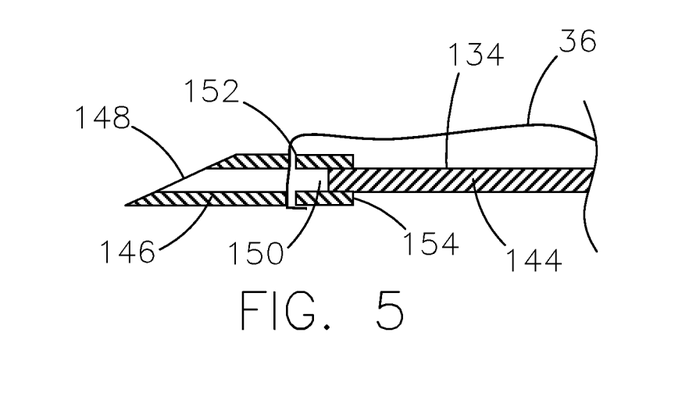
FIG. 5 is a cross-sectional view of an alternate embodiment of the needle depicted in FIG. 4.

Many variations of the needle 34 will be readily apparent to those skilled in the art, one such variation being depicted in FIG. 5. Generally, the needle 134 includes a solid shaft 144 and a hollow needle tip 146. The head 148 of the needle tip 146 is tapered to promote piercing of the tissue 12. An interior lumen 150 of the needle tip 146 is size relative to the shaft 144 to provide a friction fit and selective connection and disconnection of the needle tip 146 from the shaft 144, such as described above with regard to the embodiment of FIG. 4. A through-hole 152 is also provided in the needle tip 146, thereby allowing the suture 36 to be passed through the hole 152 and crimped, knotted, melted or otherwise deformed to connect the suture 36 to the needle tip 146.

Figure 6:
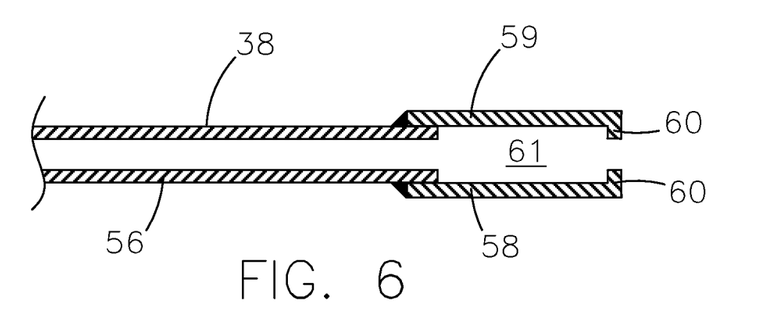
FIG. 6 is a cross-sectional view of a retrieval device from a portion of the medical system depicted in FIG. 1.
Figure 7:
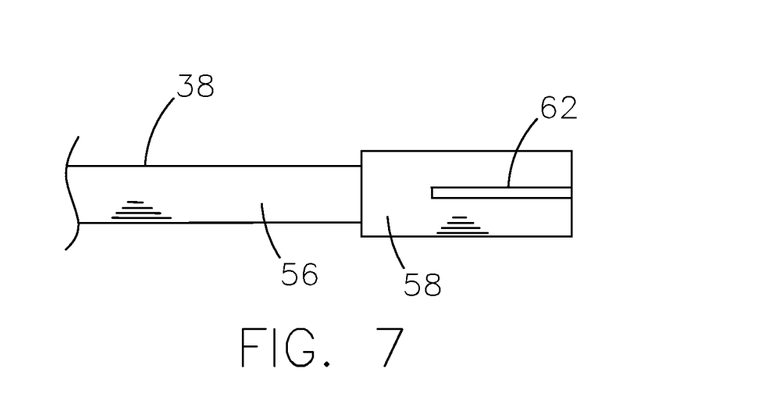
FIG. 7 is a side-view of the retrieval device depicted in FIG. 6.

FIGS. 6 and 7 depict one embodiment of a retrieval device 38 forming a portion of the medical device 24 and medical system 22. The retrieval device 38 generally includes an elongated member 56 sized to be translated through the working channel 23 of the endoscope 22. As such, the elongated member 56 has a sufficient length to pass fully through to the working channel 23 of the endoscope 22 and exit a proximal end thereof (not shown) for manipulation by the medical professional. A grasping tip 58 is connected to a distal end of the elongated member 56 for selectively engaging the needle tip 46 of the needle 34. In this embodiment, the grasping tip 58 has been shown as a tubular sleeve 59 that opens at its distal end. The sleeve 59 defines an interior passageway 61 sized to receive the needle tip 46. The distal end of the grasping tip 58 further define one or more teeth 60 for engaging a gripping surface 54 formed on the needle tip 46. As best seen in the side view of FIG. 7, the grasping tip 58 generally includes one or more slots 62 which allow the inner diameter of the sleeve 59 to expand for receiving the needle tip 46. Accordingly, the grasping tip 58 is preferably formed of a resilient material having some flexibility, such as metals, alloys (preferably super-elastic alloys such as nitinol) or suitable plastics. The elongated member 56 is preferably formed of a flexible material that can bend along with the endoscope 22 as it traverses the body of a patient and may be formed of metals, alloys such as nitinol, or suitable plastics.

Figure 8:
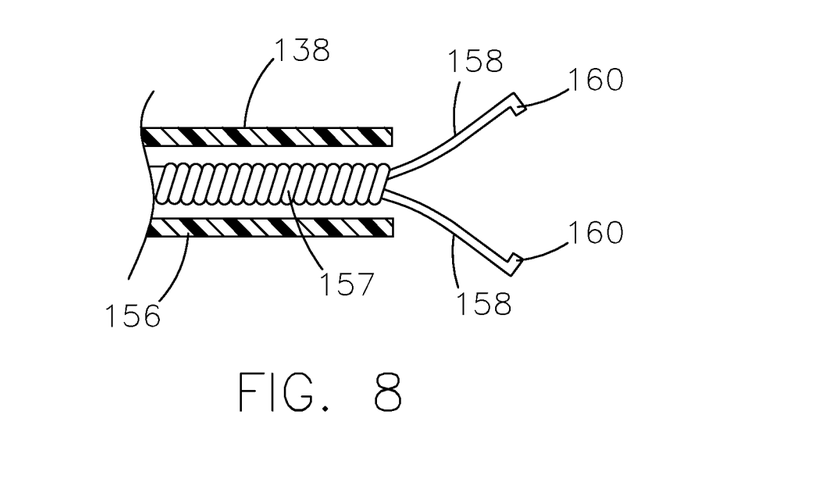
FIG. 8 is a side-view, partially and cross-section, of an alternate embodiment of the retrieval device depicted in FIG. 6.

Many different retrieval devices may be employed to form a portion of the medical system 20 and medical device 24 of the present invention. For example, forceps, snares, wire loops, graspers and magnets may be employed to engage the needle tip 46 for retrieval thereof and the suture 36. As one example, FIG. 8 depicts an alternate embodiment of a retrieval device 138 having a flexible elongated sheath 156 and a control member 157. Grasping arms 158 are attached to a distal end thereof. The grasping arms 158 define teeth 160, and are a generally biased radially outwardly as shown in the figure. The control wire 157 may be formed by a plurality of wound or braided wires, the distal ends of which may be used to form the grasping arms 158. The size and position of the grasping arms 158 is structured relative to the elongated sheath 156 such that translation of the control wire 157 relative to the sheath 156 controls operation of the grasping arms 158 between open and closed configurations. That is, a distal end of the sheath 156 will press on the grasping arms 158 to draw them together and grasp an object such as the needle tip 46. This and many other types of retrieval devices, both passive and actively operated, may be employed within the scope of the present invention.

Figure 9:
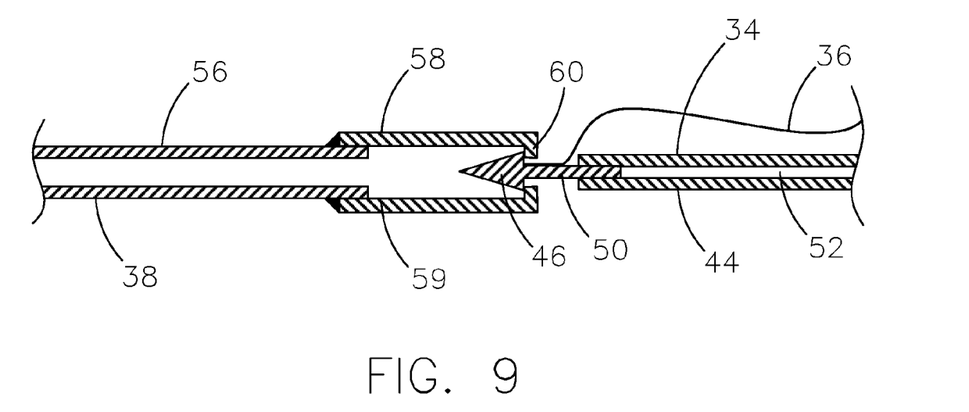
FIGS. 9 and 10 are cross-sectional views showing different stages of interaction between the needle and retrieval device depicted in FIGS. 4 and 6.
Figure 10:
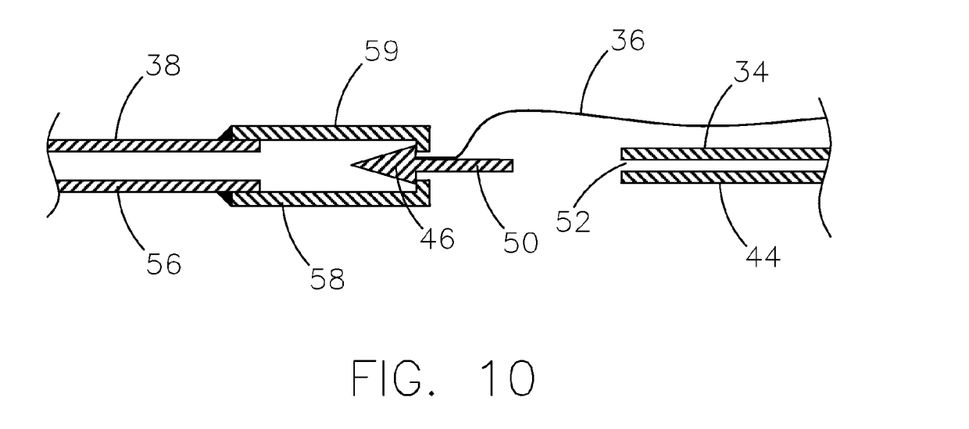

FIGS. 9 and 10 show two stages of operating the retrieval device 38 to retrieve the needle tip 46 of the needle 34. In FIG. 9, the retrieval device 38 has been translated relative to the needle 34 such that the open distal end of the grasping tip 58 passes over the needle head 48. The teeth 60 on the resilient sleeve 59 draw around the needle head 48 and engage the gripping surface 54 defined thereby. As shown in FIG. 10, the retrieval device 38 may again be translated relative to the needle 34, and in particular the shaft 44, such that the friction between the post 50 and needle lumen 52 is overcome and the needle tip 46 is disengaged from the shaft 44. It will be recognized that the relative movement between the needle 34 and retrieval device 38 as shown in FIGS. 9 and 10 may be accomplished through translation of the retrieval device 38 or translation of the needle 34 or translation of both the needle 34 and retrieval device 38.

As will now be described with reference to FIGS. 11-15, a method for employing the medical system 20 and medical device 24 for suturing a perforation 14 in tissue 12 is also provided in accordance with the teachings of the present invention. As shown in FIG. 11, the method includes providing an endoscope 22 and medical device 24, such as one of the medical devices described above. The endcap 26 of the medical device 24 is fitted to a distal end of the endoscope 22. The endoscope 22 and medical device 24 are introduced together into the body of a patient, preferably through a natural orifice such as the mouth, anus or vagina, and are translated to a position proximate the tissue 12. In procedures where a perforation in the tissue 12 is not already formed but is desired, an appropriate surgical tool such as a needle-knife or other electrocautery device, or cutting instrument may be employed through the working channel 23 or another channel of the endoscope 22 for forming the perforation 14. The endoscope 22 and medical device 24 are manipulated such that the side tube 30 is positioned proximate the perforation 14. The side tube 30 may not be visible via the endoscope 22, however its location may be identified by visualizing the slot 40 formed in the endcap 26. When no slot 40 is employed, the interior surface of the endcap 26 may include visual markings for identifying the location of the side tube 30.

Figure 12:
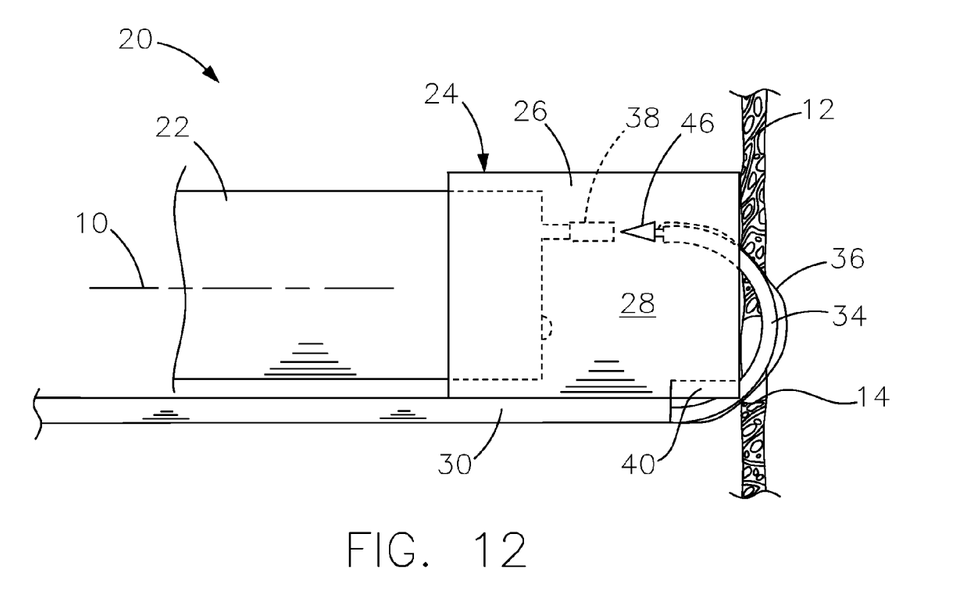

As also shown in FIG. 11, the needle 34 is loaded within the side channel 32. The needle 34 is generally operable between a delivery configuration, such as shown in FIG. 11, and a deployed configuration such as is shown in FIG. 12 (and previously in FIGS. 1-3). In the delivery configuration of the needle 34, the needle tip 46 is generally aligned with the side tube 30. The needle tip 46 moves laterally between the delivery configuration and the deployed configuration, and more particularly the distal end of the needle shaft 44 bends along a curved path and preferably retroflexes such that it is radially aligned with the retrieval device 38 and the working channel 23 of the endoscope 22. Although shown rotating about 180 degrees, the needle 34 may rotate less than or more than 180 degrees in the deployed configuration. Preferably, the needle shaft 44 is retroflexed in the deployed configuration such that the needle tip 46 faces proximally.

The needle 34 is operated from the delivery configuration to the deployed configuration as shown in FIG. 12. The needle 34 is translated distally relative to the side tube 30, and is first passed through the perforation 14 and then through the tissue 12. That is, the needle 34 is passed through the tissue 12 in a retrograde manner, i.e. from a distal side to a proximal side of the tissue 12. As shown in FIG. 12, the suture 36 attached to the needle tip 46 is likewise passed through the perforation 14 and tissue 12 for retrieval by the retrieval device 38.

Figure 13:
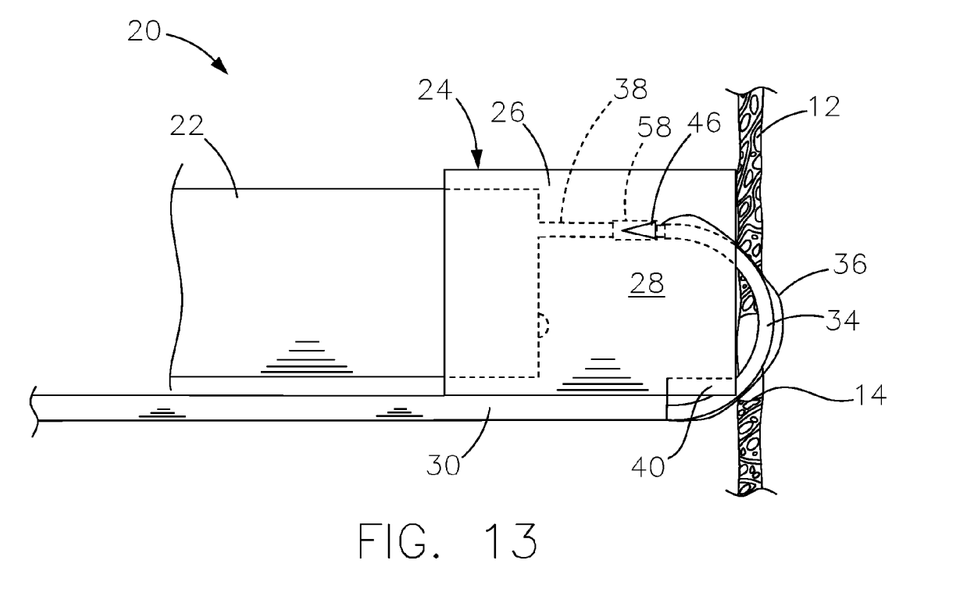
Figure 14:
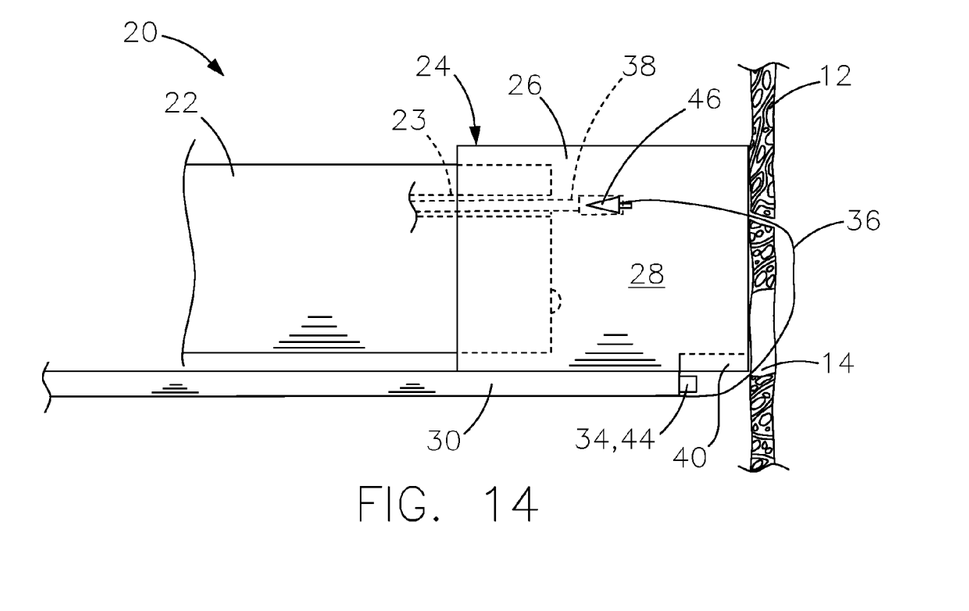

As shown in FIG. 13, the retrieval device 38 is operated to engage the needle tip 46. In particular, and as previously described with reference to FIGS. 9 and 10, the grasping tip 58 encapsulates the needle tip 46 for engagement therebetween. This interconnection may be made through distal translation of either or both the retrieval device 38 and the needle 34. As shown in FIG. 14, the needle tip 46 is then detached from the shaft 44 of the needle 34. As also previously discussed, this may be accomplished through proximal translation of either or both the retrieval device 38 and needle 34 to overcome the friction between the needle tip 46 and shaft 44. Accordingly, it can be seen that the retrieval device 38 has not only engaged the needle tip 46, but has also engaged the suture 36. As such, the retrieval device 38 may be retracted through the endoscope 22 where it and the suture 36 can be further manipulated by the medical professional.

Figure 15:
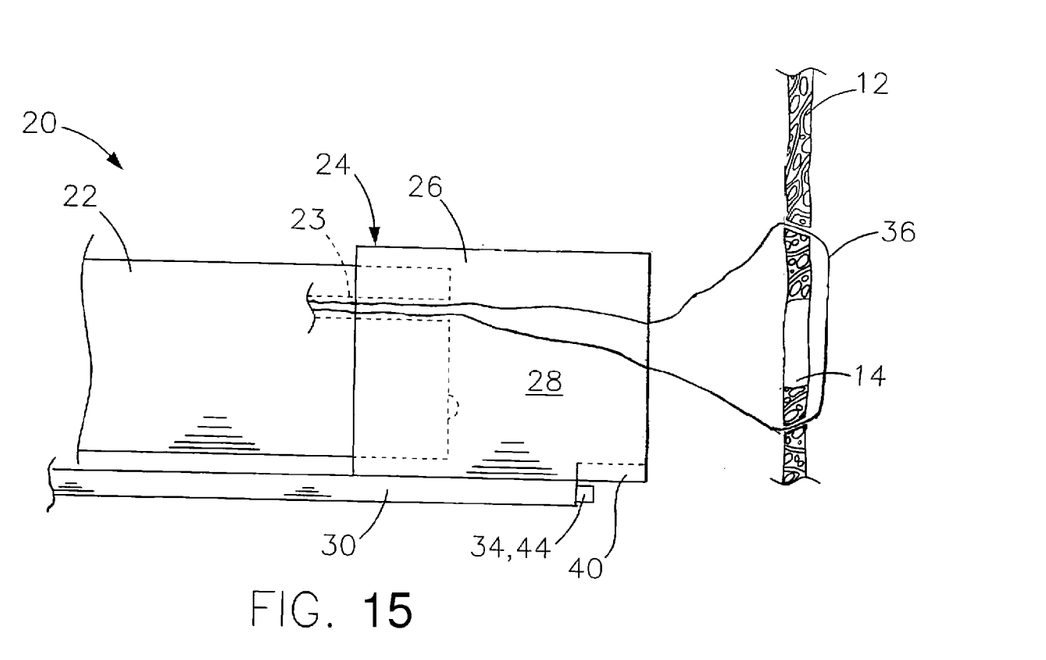
Figure 16:
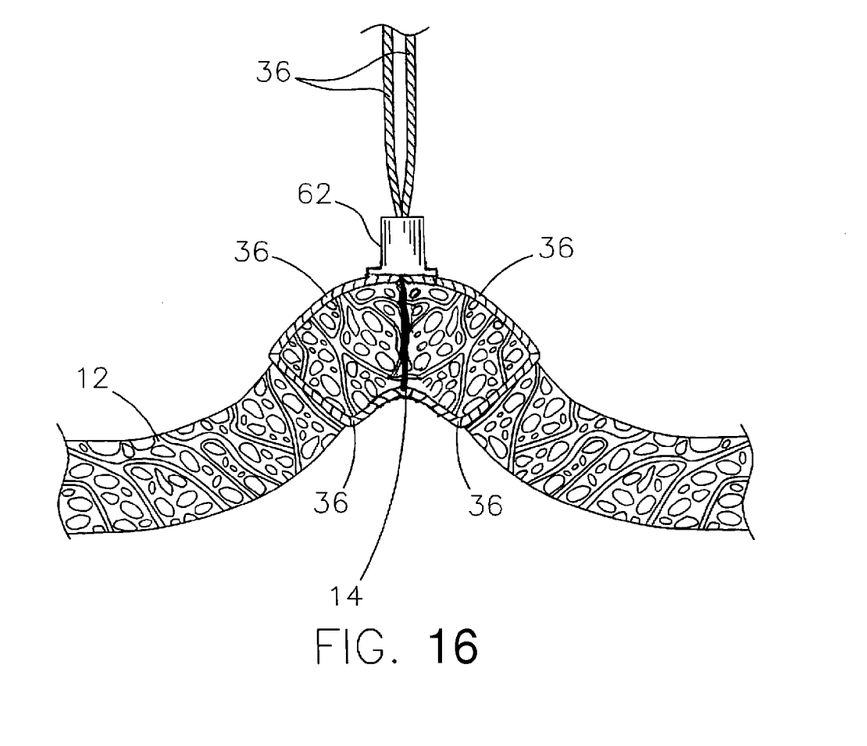
FIG. 16 is a cross-sectional view showing closure of a perforation by the medical system depicted in FIG. 1.

Upon detachment of the needle tip 46, the needle 34 (and in particular the needle shaft 44) may be withdrawn proximally through the side tube 30. The shaft 44 may be completely withdrawn through the proximal end of the side channel 32 and reloaded with a second needle tip 46 located at a second end (i.e. the formerly proximal end) of the suture 36. Since the suture 36 already extends through the side tube 30, the reloaded needle 34 and second needle tip 46 may be delivered through the side tube 30. The needle 34 and second needle tip 46 are passed through the tissue 12 in a retrograde manner as described above, and preferably on an opposite side of the perforation 14 as shown in FIG. 15. With reference to FIG. 16, the two ends of the suture 36 may be drawn together and tied to close the perforation 14, such as utilizing endoscopic tying techniques including passing knots, or through the use of a suture lock 62 as shown. Exemplary suture locks are described in U.S. patent application Ser. Nos. 12/125,525 and 12/191,001, the disclosures of which are hereby incorporated by reference in their entirety. Preferably, the ends of the suture 36 are placed on opposite sides of the perforation 14 and/or spaced around the perforation 14 to draw the tissue 12 together and securely close the perforation 14 to promote healing of the tissue 12.

In alternate methods, the suture 36 could initially be positioned outside of the side tube 30. In one such method, once the first end of the suture 36 is placed through the tissue 12 in a retrograde manner (as described above) the entire endoscope 22 and medical device 24 may be removed from the accessed bodily lumen of the patent. Upon removal, the second end of the suture 36 (having a detachable needle tip 46) may be loaded on the distal end of the needle 34, and the endoscope 22 and device 24 replaced into the bodily lumen for placement of the second end of the suture 36. In another such method, after the first end of the suture 36 has been placed, the second end of the suture 36 could simply be retained outside of the patient. A second suture 36 having a detachable needle tip 46 can be loaded onto the needle 34 and the second suture 36 may be placed as described above.

It will be recognized by those skilled in the art that the medical systems, devices and methods of the present invention facilitate improved closure of perforations. The medical systems and devices are simple to operate, and the methods may be performed endoscopically and/or laparoscopically. The devices and methods offer reliable and controllable placement of sutures around a perforation for complete closure thereof.

It will also be recognized by those skilled in the art that, while the methods described above generally include placing the tissue devices in tissue through an internal bodily lumen, it will be recognized that the systems, devices and methods may be used on any layer of material (e.g. fabrics, cloth, polymers, elastomers, plastics and rubber) that may or may not be associated with a human or animal body and a bodily lumen. For example, the systems, devices and methods can find use in laboratory and industrial settings for placing devices through one or more layers of material that may or may not find application to the human or animal body, and likewise closing holes or perforations in layers of material that are not bodily tissue. Some examples include sewing or stitching and related manufacturing, working with synthetic tissues, connecting or repairing polymeric sheets, animal studies, and post-mortem activities.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for use with an endoscope to suture a perforation in tissue, the medical device comprising:
   an endcap having a side wall defining an interior space sized to receive a distal end of the endoscope;
   an elongated side tube defining a side channel, the side tube directly connected to the exterior of the endcap;
   a needle having a shaft and a needle tip detachably connected to a distal end of the shaft, the needle sized to be translated through the side channel, the needle being operable to a deployed configuration, the needle tip being laterally spaced from the side tube in the deployed configuration;
   a distal end of the endcap opening longitudinally and having a flange extending radially inward to define a tissue support surface that is sized and positioned to support the tissue adjacent the needle as it moves to the deployed configuration, the tissue support surface being co-planar with a distal end surface of the end cap;
   a suture attached to the needle tip; and
   a retrieval device sized to be translated through a working channel of the endoscope for retrieval of the suture and needle tip.

2. The medical of claim 1, wherein the distal end of the needle shaft bends along a curved path in the deployed configuration.

3. The medical device of claim 1, the endoscope defining a central axis, and wherein the needle tip and retrieval device are radially aligned relative to the central axis in the deployed configuration.

4. The medical device of claim 3, wherein the distal end of the needle shaft has a curvature such that the needle tip faces proximally in the deployed configuration.

5. The medical device of claim 1, wherein the retrieval device includes a resilient sleeve having teeth, the sleeve defining an interior passageway sized to receive the needle tip.

6. The medical device of claim 5, wherein the needle tip defines a gripping surface, and wherein the teeth are sized and structured to engage the gripping surface.

7. The medical device of claim 1, wherein the interior space is sized to provide selective frictional engagement between the endcap and the endoscope.

8. The medical device of claim 1, wherein a distal portion of the endcap includes a slot extending through the sidewall to the exterior and circumferentially aligned with the side tube.

9. The medical device of claim 1, wherein the flange is positioned proximate the needle when the needle is in the deployed configuration.

10. The medical device of claim 1, wherein the needle is operable to a delivery configuration, the needle tip being aligned with the side tube in the delivery configuration.

11. The medical device of claim 1, wherein the side tube extends along the exterior of the endoscope.

12. The medical device of claim 1, wherein the side tube is connected to the endcap on a first side of the endcap, and wherein the flange extends inward from a second side of the endcap opposite the first side.

13. The medical device of claim 1, wherein the retrieval device is elongated and structured to longitudinally slide through the working channel.

\* \* \* \* \*